United States Patent
Desenne et al.

(10) Patent No.: US 9,149,418 B2
(45) Date of Patent: *Oct. 6, 2015

(54) COSMETIC COMPOSITION IN THE FORM OF A NANOEMULSION CONTAINING A VOLATILE LINEAR ALKANE

(75) Inventors: Patricia Desenne, Pringy (FR); Laurent Chesneau, Levallois (FR)

(73) Assignee: L'OREAL, Paris (FR)

( * ) Notice: Subject to any disclaimer, the term of this patent is extended or adjusted under 35 U.S.C. 154(b) by 216 days.

This patent is subject to a terminal disclaimer.

(21) Appl. No.: 12/977,257

(22) Filed: Dec. 23, 2010

(65) Prior Publication Data

US 2011/0150813 A1 Jun. 23, 2011

Related U.S. Application Data

(60) Provisional application No. 61/296,493, filed on Jan. 20, 2010.

(30) Foreign Application Priority Data

Dec. 23, 2009 (FR) ...................... 09 59480

(51) Int. Cl.
*A61K 8/92* (2006.01)
*A61Q 5/12* (2006.01)
*A61K 8/06* (2006.01)
*A61K 8/31* (2006.01)
*A61K 8/39* (2006.01)

(52) U.S. Cl.
CPC . *A61K 8/06* (2013.01); *A61K 8/062* (2013.01); *A61K 8/31* (2013.01); *A61K 8/39* (2013.01); *A61K 8/922* (2013.01); *A61Q 5/12* (2013.01); *A61K 2800/21* (2013.01)

(58) Field of Classification Search
CPC ....... A61Q 19/00; A61Q 17/04; A61Q 15/00; A61Q 1/00; A61Q 19/10; A61Q 1/06; A61Q 1/10; A61Q 1/14; A61Q 5/00; A61Q 5/06; A61Q 5/12
See application file for complete search history.

(56) References Cited

U.S. PATENT DOCUMENTS

| | | | | |
|---|---|---|---|---|
| 4,374,825 A | * | 2/1983 | Bolich et al. | 424/70.12 |
| 4,886,660 A | * | 12/1989 | Patel et al. | 424/70.13 |
| 2001/0028887 A1 | * | 10/2001 | Douin et al. | 424/401 |
| 2005/0287088 A1 | * | 12/2005 | Guiramand et al. | 424/59 |
| 2007/0178144 A1 | | 8/2007 | Hameyer et al. | |
| 2008/0269352 A1 | * | 10/2008 | Falkowski et al. | 514/762 |

FOREIGN PATENT DOCUMENTS

| | | |
|---|---|---|
| DE | 10 2008 012 457 | 12/2008 |
| EP | 1 813 251 | 8/2007 |
| EP | 2 113 240 | 11/2009 |

OTHER PUBLICATIONS

Anonymous, "Paraffine," Wikipedia Encylcopedia, XP002602767, Sep. 23, 2010.
French Search Report, issued Sep. 29, 2010, in FR 09 59480, filed Dec. 23, 2009.
Anonymous, "Paraffine," Wikipedia Encylcopedia, Sep. 23, 2010.
U.S. Appl. No. 12/977,183, filed Dec. 23, 2010, Desenne et al.
U.S. Appl. No. 12/969,980, filed Dec. 16, 2010, Desenne et al.
U.S. Appl. No. 12/975,705, filed Dec. 22, 2010, Desenne et al.
U.S. Appl. No. 12/970,988, filed Dec. 17, 2010, Desenne et al.
U.S. Appl. No. 12/977,204, filed Dec. 23, 2010, Desenne et al.
U.S. Appl. No. 12/977,227, filed Dec. 23, 2010, Desenne et al.
U.S. Appl. No. 12/975,632, filed Dec. 22, 2010, Desenne et al.

* cited by examiner

*Primary Examiner* — Audrea Buckley
(74) *Attorney, Agent, or Firm* — Oblon, McClelland, Maier & Neustadt, L.L.P.

(57) ABSTRACT

Composition in the form of an oil-in-water nanoemulsion containing one or more nonionic amphiphilic lipids, one or more volatile linear alkanes and one or more oils other than the volatile linear alkane(s).

14 Claims, No Drawings

COSMETIC COMPOSITION IN THE FORM OF A NANOEMULSION CONTAINING A VOLATILE LINEAR ALKANE

REFERENCE TO PRIOR APPLICATIONS

This application claims priority to U.S. provisional application Ser. No. 61/296,493, filed Jan. 20, 2010; and to French patent application 09 59480, filed Dec. 23, 2009, both incorporated herein by reference.

FIELD OF THE INVENTION

The present invention relates to a cosmetic composition in the form of an oil-in-water nanoemulsion comprising, preferably in a cosmetically acceptable medium, at least one volatile linear alkane, at least one oil and at least one nonionic amphiphilic lipid preferably in a particular oil/nonionic amphiphilic lipid ratio, and also to its use for conditioning the hair.

BACKGROUND OF THE INVENTION

In the cosmetics field, nanoemulsions of oil-in-water type are known for their conditioning properties, such as the disentangling and smoothing of hair, without loss of tonicity of the fibre.

However, they are fluid systems that are difficult to stabilize without degrading the level of the conditioning properties.

Moreover, it is known practice to use volatile solvents in rinse-out or leave-in haircare products. These volatile solvents generally make it possible to modify the sensory feel of a hair product by lightening its texture. They can also give it a fondant nature that facilitates its application to the hair.

However, volatile solvents, such as liquid fatty esters, hydrocarbon-based oils of isododecane or isohexadecane type, or silicone oils of cyclomethicone type, do not afford any particular thickening in a nanoemulsion.

There is thus a need for a cosmetic composition in nanoemulsion form that has a thickened consistency, i.e. which can be in gel form, while at the same time having satisfactory conditioning properties, in particular in terms of softness, sheen and lightness.

DETAILED DESCRIPTION OF THE PREFERRED EMBODIMENTS

It has now been discovered, surprisingly, that a composition in the form of an oil-in-water nanoemulsion comprising at least one volatile linear alkane, at least one oil other than the volatile linear alkane(s) and at least one nonionic amphiphilic lipid makes it possible to solve the problems of the prior art and to give the desired effects mentioned previously.

Thus, one subject of the invention is a cosmetic composition in the form of an oil-in-water nanoemulsion comprising, preferably in a cosmetically acceptable medium, one or more nonionic amphiphilic lipids, one or more volatile linear alkanes and one or more oils other than the volatile linear alkane(s).

Preferably, the weight ratio of the amount of oil(s) to the amount of nonionic amphiphilic lipid(s) is less than or equal to 7.

For the purposes of the present invention, the term "nanoemulsion" means an oil-in-water emulsion characterized by an oil globule size of less than 350 nm, the oil globules being stabilized by a crown of amphiphilic lipids that may optionally form a liquid crystal phase of lamellar type, at the oil/aqueous phase interface. In the absence of specific opacifiers, the transparency of these emulsions arises from the small size of the oil globules, this small size being obtained by virtue of the use of mechanical energy and especially a high-pressure homogenizer. Nanoemulsions are distinguished from microemulsions by their structure. Specifically, microemulsions are thermodynamically stable dispersions formed from amphiphilic lipid micelles swollen with oil. Furthermore, microemulsions do not require substantial mechanical energy in order to be prepared; they are formed spontaneously by simply placing the constituents in contact.

Preferably, the nanoemulsions of the invention contain globules with a number-average size of between 1 and 350 nm, better still between 5 and 250 nm and even more preferentially between 10 and 150 nm.

The number-average size of the globules may be determined in particular according to the known method of quasi-elastic light scattering. As a machine that may be used for this determination, mention may be made of the Brookhaven brand machine equipped with an SX 200 optical bed (with a 532 nm laser) and a BI 9000 correlator. This machine gives a measurement of the mean diameter by photon correlation spectroscopy (PCS), which makes it possible to determine the number-average diameter from the polydispersity factor, which is also measured by the machine.

The nanoemulsion may also be characterized by measuring its turbidity according to the NTU method using a 2100P model turbidimeter from the company Hach, at room temperature. The turbidity of the nanoemulsions of the invention is generally less than 400 NTU units, preferably between 10 and 300, better still from 15 to 250 and more particularly from 20 to 150 NTU units.

The turbidity of the emulsions may also be measured by measuring the transmittance at 600 nm. The transmittance is generally greater than 85%, preferably greater than 90% and more particularly greater than 94%.

The composition according to the invention contains one or more volatile linear alkane(s). The term "one or more volatile linear alkane(s)" means, without preference, "one or more volatile linear alkane oil(s)".

A volatile linear alkane that is suitable for use in the invention is liquid at room temperature (about 25° C.) and at atmospheric pressure (760 mmHg).

The term "volatile linear alkane that is suitable for use in the invention" means a cosmetic linear alkane that can evaporate on contact with the skin in less than one hour, at room temperature (25° C.) and atmospheric pressure (760 mmHg, i.e. 101 325 Pa), which is liquid at room temperature, especially having an evaporation rate ranging from 0.01 to 15 mg/cm2/minute, at room temperature (25° C.) and atmospheric pressure (760 mmHg).

Preferably, the volatile linear alkane(s) that are suitable for use in the invention have an evaporation rate ranging from 0.01 to 3.5 mg/cm2/minute, at room temperature (25° C.) and atmospheric pressure (760 mmHg).

Preferably, the volatile linear alkane(s) that are suitable for use in the invention have an evaporation rate ranging from 0.01 to 1.5 mg/cm2/minute, at room temperature (25° C.) and atmospheric pressure (760 mmHg).

More preferably, the volatile linear alkane(s) that are suitable for use in the invention have an evaporation rate ranging from 0.01 to 0.8 mg/cm2/minute, at room temperature (25° C.) and atmospheric pressure (760 mmHg).

Even more preferably, the volatile linear alkane(s) that are suitable for use in the invention have an evaporation rate ranging from 0.01 to 0.3 mg/cm2/minute, at room temperature (25° C.) and atmospheric pressure (760 mmHg).

Even more preferably, the volatile linear alkane(s) that are suitable for use in the invention have an evaporation rate ranging from 0.01 to 0.12 mg/cm2/minute, at room temperature (25° C.) and atmospheric pressure (760 mmHg).

The evaporation rate of a volatile alkane in accordance with the invention (and more generally of a volatile solvent) may especially be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m3 with regulated temperature (25° C.) and hygrometry (50% relative humidity).

The liquid is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm2) as a function of the time (in minutes).

The evaporation rate is then calculated, which corresponds to the tangent to the origin of the curve obtained. The evaporation rates are expressed in mg of volatile solvent evaporated per unit surface area (cm2) and per unit of time (minutes).

According to one preferred embodiment, the volatile linear alkane(s) that are suitable for use in the invention have a non-zero vapour pressure (also known as the saturating vapour pressure), at room temperature, in particular a vapour pressure ranging from 0.3 Pa to 6000 Pa.

Preferably, the volatile linear alkane(s) that are suitable for use in the invention have a vapour pressure ranging from 0.3 to 2000 Pa, at room temperature (25° C.).

Preferably, the volatile linear alkane(s) that are suitable for use in the invention have a vapour pressure ranging from 0.3 to 1000 Pa, at room temperature (25° C.).

More preferably, the volatile linear alkane(s) that are suitable for use in the invention have a vapour pressure ranging from 0.4 to 600 Pa, at room temperature (25° C.).

Preferably, the volatile linear alkane(s) that are suitable for use in the invention have a vapour pressure ranging from 1 to 200 Pa, at room temperature (25° C.).

More preferably, the volatile linear alkane(s) that are suitable for use in the invention have a vapour pressure ranging from 3 to 60 Pa, at room temperature (25° C.).

According to one embodiment, the volatile linear alkane(s) that are suitable for use in the invention may have a flash point that is within the range from 30 to 120° C. and more particularly from 40 to 100° C. The flash point is in particular measured according to standard ISO 3679.

According to one embodiment, the volatile linear alkane(s) that are suitable for use in the invention may be linear alkanes comprising from 7 to 15 carbon atoms.

Preferably, the volatile linear alkane(s) that are suitable for use in the invention may be linear alkanes comprising from 8 to 14 carbon atoms.

Preferably, the volatile linear alkane(s) that are suitable for use in the invention may be linear alkanes comprising from 9 to 14 carbon atoms.

Preferably, the volatile linear alkane(s) that are suitable for use in the invention may be linear alkanes comprising from 10 to 14 carbon atoms.

Preferably, the volatile linear alkane(s) that are suitable for use in the invention may be linear alkanes comprising from 11 to 14 carbon atoms.

According to one advantageous embodiment, the volatile linear alkane(s) that are suitable for use in the invention have an evaporation rate, as defined above, ranging from 0.01 to 3.5 mg/cm2/minute, at room temperature (25° C.) and atmospheric pressure (760 mmHg), and comprise from 8 to 14 carbon atoms.

The volatile linear alkane(s) that are suitable for use in the invention may advantageously be of plant origin.

Preferably, the volatile linear alkane or the mixture of volatile linear alkanes present in the composition according to the invention comprises at least one 14C (carbon-14) carbon isotope. In particular, the 14C isotope may be present in a 14C/12C ratio of greater than or equal to $1 \times 10^{-16}$, preferably greater than or equal to $1 \times 10^{-15}$, more preferably greater than or equal to $7.5 \times 10^{-14}$ and better still greater than or equal to $1.5 \times 10^{-13}$. Preferably, the ratio 14C/12C ranges from $6 \times 10^{-13}$ to $1.2 \times 10^{-12}$ (numerical isotope ratio).

The amount of 14C isotopes in the volatile linear alkane or the mixture of volatile linear alkanes may be determined via methods known to those skilled in the art such as the Libby counting method, liquid scintillation spectrometry or accelerator mass spectrometry.

Such an alkane may be obtained, directly or in several steps, from a plant raw material, such as an oil, a butter, a wax, etc.

As examples of volatile linear alkanes that are suitable for use in the invention, mention may be made of the alkanes described in patents WO 2007/068 371 or WO 2008/155 059 of the company Cognis (mixtures of different alkanes differing by at least one carbon). These alkanes are obtained from fatty alcohols, which are themselves obtained from coconut oil or palm oil.

As examples of volatile linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to one particular embodiment, the volatile linear alkane is chosen from n-nonane, n-undecane, n-dodecane, n-tridecane and n-tetradecane, and mixtures thereof.

According to one preferred mode, mention may be made of mixtures of n-undecane (C11) and of n-tridecane (C13) obtained in Examples 1 and 2 of patent application WO 2008/155 059 of the company Cognis.

Mention may also be made of n-dodecane (C12) and n-tetradecane (C14) sold by Sasol under the references, respectively, Parafol 12-97 and Parafol 14-97, and also mixtures thereof.

The volatile linear alkane may also be used alone.

Alternatively or preferentially, a mixture of two different volatile linear alkanes, differing from each other by a carbon number n of at least 1, in particular differing from each other by a carbon number of 1 or 2, may be used.

According to one embodiment, a mixture of at least two different volatile linear alkanes comprising from 10 to 14 carbon atoms and differing from each other by a carbon number of at least 1 is used. Examples that may especially be mentioned include mixtures of C10/C11, C11/C12 or C12/C13 volatile linear alkanes.

According to another embodiment, a mixture of at least two different volatile linear alkanes comprising from 10 to 14 carbon atoms and differing from each other by a carbon number of at least 2 is used. Examples that may especially be mentioned include mixtures of C10/C12 or C12/C14 volatile linear alkanes, for an even carbon number n, and the C11/C13 mixture for an odd carbon number n.

According to one preferred mode, a mixture of at least two different volatile linear alkanes comprising from 10 to 14 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes comprising from 7 to 15 carbon atoms and differing from each other by a carbon number of at least 1, also form part of the invention, but mixtures of two volatile linear alkanes according to the invention are preferred (binary mixtures), the two volatile linear alkanes preferably representing more than 95% and better still more than 99% by weight of the total content of volatile linear alkanes in the mixture.

According to one particular mode of the invention, in a mixture of volatile linear alkanes, the volatile linear alkane having the smaller carbon number is predominant in the mixture.

According to another mode of the invention, a mixture of volatile linear alkanes in which the volatile linear alkane having the larger carbon number is predominant in the mixture is used.

As examples of mixtures that are suitable for use in the invention, mention may be made especially of the following mixtures:

- from 50% to 90% by weight, preferably from 55% to 80% by weight and more preferentially from 60% to 75% by weight of Cn volatile linear alkane with n ranging from 7 to 15,
- from 10% to 50% by weight, preferably from 20% to 45% by weight and preferably from 24% to 40% by weight of Cn+x volatile linear alkane with x greater than or equal to 1, preferably x=1 or x=2, with n+x between 8 and 14, relative to the total weight of alkanes in the mixture.

In particular, the mixture of volatile linear alkanes according to the invention may also contain:

- less than 2% by weight and preferably less than 1% by weight of branched hydrocarbons,
- and/or less than 2% by weight and preferably less than 1% by weight of aromatic hydrocarbons,
- and/or less than 2% by weight, preferably less than 1% by weight and preferentially less than 0.1% by weight of unsaturated hydrocarbons in the mixture.

More particularly, a volatile linear alkane that is suitable for use in the invention may be used in the form of an n-undecane/n-tridecane mixture.

In particular, a mixture of volatile linear alkanes will be used comprising:

- from 55% to 80% by weight and preferably from 60% to 75% by weight of C11 volatile linear alkane (n-undecane),
- from 20% to 45% by weight and preferably from 24% to 40% by weight of C13 volatile linear alkane (n-tridecane),
- relative to the total weight of alkanes in the mixture.

According to one particular embodiment, the mixture of alkanes is an n-undecane/n-tridecane mixture. In particular, such a mixture may be obtained according to Example 1 or Example 2 of WO 2008/155 059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and n-tetradecane is used. It is in particular possible to use the dodecane/tetradecane mixture in an 85/15 weight ratio sold by the company Biosynthis under the reference Vegelight 1214.

The volatile linear alkane(s) preferably represent from 0.5% to 50% by weight of volatile linear alkanes, in particular from 1% to 30% by weight and more particularly from 2% to 15% by weight relative to the total weight of the composition.

The volatile linear alkane(s) form, alone or with one or more other compounds listed below, the liquid fatty phase of the composition.

As explained previously, the composition according to the invention comprises, besides the volatile linear alkane(s), one or more oils other than these volatile linear alkanes.

The term "oil" means any non-aqueous medium that is liquid at room temperature (25° C.±3° C.) and at atmospheric pressure (760 mmHg), with a solubility in water at 25° C. of less than 1% by weight and preferably less than 0.5% by weight. The oils used according to the present invention preferably comprise at least one chain comprising at least six carbon atoms or at least two siloxane groups and preferably do not contain any carboxylic acid functions COOH.

The oils that may be used in the present invention are all oils corresponding to this definition. They may be chosen especially from plant oils, animal oils, mineral oils, synthetic oils, liquid fatty alcohols and silicone oils, and mixtures thereof.

Plant oils that may especially be mentioned include sweet almond oil, argan oil, avocado oil, groundnut oil, camellina oil, safflower oil, beauty-leaf oil, rapeseed oil, coconut oil, coriander oil, marrow oil, wheat germ oil, jojoba oil or liquid jojoba wax, linseed oil, macadamia oil, corn germ oil, hazelnut oil, walnut oil, vernonia oil, apricot kernel oil, olive oil, evening-primrose oil, palm oil, passion flower oil, grapeseed oil, rose oil, castor oil, rye oil, sesame oil, rice bran oil, soybean oil and sunflower oil.

An animal oil that may especially be mentioned is perhydrosqualene.

A liquid paraffin or a liquid petroleum jelly may be used as mineral oil.

Synthetic oils that may especially be used include fatty esters, fatty ethers, squalane, poly($\alpha$-olefins), for instance polydecenes and polyisobutenes, transesterified plant oils and halogenated oils, especially fluoro oils.

Olive oil transesterified with hexanol or jojoba wax transesterified with ethanol may be used as transesterified plant oil.

Examples of fluoro oils that may also be mentioned include perfluoromethylcyclopentane and perfluoro-1,3-dimethylcyclohexane, sold under the names Flutec PC1® and Flutec PC3® by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane sold under the name MSX 4518® by the company 3M and nonafluoroethoxyisobutane; perfluoromorpholine derivatives, such as the 4-trifluoromethylperfluoromorpholine sold under the name PF 5052® by the company 3M; partially hydrocarbon-based fluoro oils, for instance those described in document JP-A-2 295 912.

The fatty esters that may be used as synthetic oils may be esters of monoalcohols or of polyols with mono- or polyacids, the total number of carbon atoms in the ester being greater than or equal to 10.

Preferably, at least one of the alcohols and/or acids comprises at least one chain of more than 7 carbon atoms.

Fatty esters that are more preferentially used are the compounds of formula RaCOORb in which Ra represents a linear or branched, hydroxylated or non-hydroxylated, saturated or unsaturated higher fatty acid residue containing from 4 to 29 carbon atoms and Rb represents a linear or branched, saturated or unsaturated hydrocarbon-based chain containing from 3 to 30 carbon atoms, the total number of carbon atoms in the ester being greater than 10. Examples that may especially be mentioned include purcellin oil (stearyl octanoate), isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, isostearyl neopentanoate and tridecyl neopentanoate.

The fatty ethers that may be used as synthetic oils are especially the compounds of formula RaORb in which Ra and Rb have the meanings given above, the total number of carbon atoms in the ether being greater than 10.

The fatty alcohols that may be used as oils are especially liquid fatty alcohols containing from 8 to 26 carbon atoms, for instance octyldodecanol, 2-butyloctanol, oleyl alcohol, linoleyl alcohol or linolenyl alcohol.

Silicone oils that may be mentioned include polyorganosiloxanes, especially as defined in Walter Noll's Chemistry and Technology of Silicones (1968) Academic Press. They may be volatile or non-volatile.

The volatile polyorganosiloxanes may be chosen from those having a boiling point of between 60° C. and 260° C., and even more particularly from:

(i) cyclic silicones containing from 3 to 7 and preferably 4 to 5 silicon atoms. These are, for example, octamethylcyclotetrasiloxane sold in particular under the name Volatile Silicone 7207 by Union Carbide or Silbione 70045 V 2 by Rhodia, decamethylcyclopentasiloxane sold under the name Volatile Silicone 7158 by Union Carbide, and Silbione 70045 V 5 by Rhodia, and mixtures thereof.

Mention may also be made of cyclocopolymers of the dimethylsiloxane/methylalkylsiloxane type, such as Volatile Silicone FZ 3109 sold by the company Union Carbide, having the chemical structure:

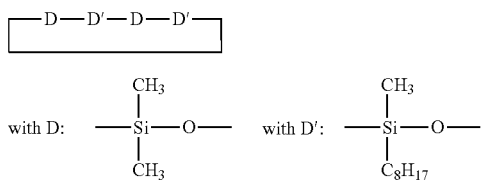

Mention may also be made of mixtures of cyclic silicones with organosilicon compounds, such as the mixture of octamethylcyclotetrasiloxane and tetratrimethylsilyl-pentaerythritol (50/50) and the mixture of octamethylcyclotetrasiloxane and oxy-1,1'-bis-(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m2/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, Volatile Silicone Fluids for Cosmetics.

The non-volatile polyorganosiloxanes may be chosen from polyalkylsiloxanes, polyarylsiloxanes, polyalkylarylsiloxanes, polyorganosiloxanes modified with organofunctional groups, polysiloxane(A)-polyoxyalkylene(B) linear block copolymers of (A-B)n type with n>3; grafted silicone polymers, with a nonsilicone organic skeleton, consisting of an organic main chain formed from organic monomers not comprising silicone, onto which are grafted, within said chain and also optionally on at least one of its ends, at least one polysiloxane macromonomer; grafted silicone polymers, with a polysiloxane skeleton grafted with non-silicone organic monomers, comprising a polysiloxane main chain onto which are grafted, within said chain and also optionally on at least one of its ends, at least one organic macromonomer not comprising silicone; and also mixtures thereof.

Examples of polyalkylsiloxanes that may especially be mentioned include polydimethylsiloxanes containing trimethylsilyl end groups with a viscosity of from $5 \times 10^{-6}$ to 2.5 m2/s at 25° C. and preferably $1 \times 10^{-5}$ to 1 m2/s. The viscosity of the silicones is measured, for example, at 25° C. according to ASTM standard 445 Appendix C.

Among these polyalkylsiloxanes, mention may be made, in a nonlimiting manner, of the following commercial products:
the Silbione oils of the 47 and 70 047 series or the Mirasil oils sold by Rhône-Poulenc, for instance the oil 70 047 V 500 000;
the oils of the Mirasil series sold by the company Rhone-Poulenc;
the oils of the 200 series from the company Dow Corning, such as, more particularly, DC200 with a viscosity of 60 000 cSt;
the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhone-Poulenc.

The polyalkylarylsiloxanes are chosen particularly from linear and/or branched polydimethylmethylphenylsiloxanes or polydimethyldiphenylsiloxanes, with a viscosity of from $1 \times 10^{-5}$ to $5 \times 10^{-2}$ m2/s at 25° C.

Among these polyalkylarylsiloxanes, mention may be made, by way of example, of the products sold under the following names:
the Silbione oils of the 70 641 series from Rhône-Poulenc;
the oils of the Rhodorsil 70 633 and 763 series from Rhone-Poulenc;
the oil Dow Corning 556 Cosmetic Grade Fluid from Dow Corning;
certain oils of the SF series from General Electric, such as SF 1023, SF 1154, SF 1250, SF 1265.

Silicone oils that may also be used include organomodified silicones, which are silicones as defined previously, comprising in their structure one or more organofunctional groups attached via a hydrocarbon-based group.

Among the organomodified silicones that may be used according to the invention, mention may be made of polyorganosiloxanes comprising:
substituted or unsubstituted amine groups;
thiol groups;
alkoxy groups;
hydroxyl groups;
acyloxyalkyl groups;
hydroxyacylamino groups.

The oils that are particularly preferred in the composition according to the invention are especially plant oils, and more particularly olive oil and liquid jojoba wax; silicone oils and more particularly linear or cyclic polydimethylsiloxanes; and mineral oils especially such as liquid petroleum jelly.

The oil(s) are advantageously present in the composition according to the invention in an amount ranging from 1% to 40% by weight and preferably from 2% to 15% by weight relative to the total weight of the composition.

As explained previously, the composition according to the invention comprises one or more nonionic amphiphilic lipids (or surfactants).

In the present patent application, the terms "amphiphilic lipid" and "surfactant" will be used interchangeably.

The nonionic amphiphilic lipids of the invention are preferentially chosen from:

1) silicone surfactants,
2) amphiphilic lipids that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, and polyglycerols comprising from 2 to 15 glycerol units, and of at least one fatty acid comprising at least one saturated or unsaturated, linear or branched C8-C22 alkyl chain,
3) mixed esters of C8-C22 fatty acid or of C8-C22 fatty alcohol, of carboxylic acid and of glycerol,
4) fatty acid esters of sugars and fatty alkyl ethers of sugars,
5) surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters,
6) block copolymers of ethylene oxide (A) and of propylene oxide (B).

1) The silicone surfactants that may be used according to the invention are silicone compounds comprising at least one oxyethylene —OCH2CH2- and/or oxypropylene —OCH2CH2CH2- chain. As silicone surfactants that may be used according to the present invention, mention may be made of those described in documents U.S. Pat. No. 5,364,633 and U.S. Pat. No. 5,411,744.

Preferably, the silicone surfactant used according to the present invention may be a compound of formula (I):

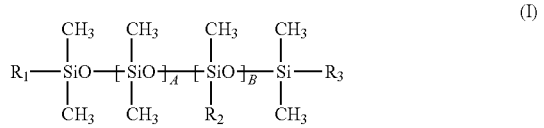

(I)

in which:
R1, R2 and R3, independently of each other, represent a C1-C6 alkyl radical or a radical —(CH2)x-(OCH2CH2)y-(OCH2CH2CH2)z-OR4, at least one radical R1, R2 or R3 not being an alkyl radical; R4 being a hydrogen, a C1-C6 alkyl radical or an acyl radical;
A is an integer ranging from 0 to 200;
B is an integer ranging from 0 to 50; with the condition that A and B are not simultaneously equal to zero;
x is an integer ranging from 1 to 6;
y is an integer ranging from 1 to 30;
z is an integer ranging from 0 to 5.

According to one preferred embodiment of the invention, in the compound of formula (I), the alkyl radical is a methyl radical, x is an integer ranging from 2 to 6 and y is an integer ranging from 4 to 30.

Examples of silicone surfactants of formula (I) that may be mentioned include the compounds of formula (II):

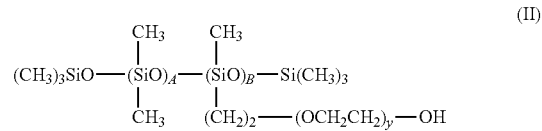

(II)

in which A is an integer ranging from 20 to 105, B is an integer ranging from 2 to 10 and y is an integer ranging from 10 to 20.

Examples of silicone surfactants of formula (I) that may also be mentioned include the compounds of formula (III):

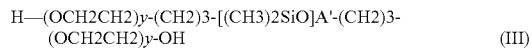

H—(OCH2CH2)y-(CH2)3-[(CH3)2SiO]A'-(CH2)3-(OCH2CH2)y-OH    (III)

in which A' and y are integers ranging from 10 to 20.

Silicone surfactants such as those sold by the company Dow Corning under the names DC 5329, DC 7439-146, DC 2-5695 and Q4-3667 may be used in particular. The compounds DC 5329, DC 7439-146 and DC2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

2) The amphiphilic lipids that are fluid at a temperature of less than or equal to 45° C. are especially:
polyethylene glycol isostearate of molecular weight 400, sold under the name PEG 400 by the company Uniqema,
diglyceryl isostearate, especially the product sold by the company Solvay;
glyceryl laurate comprising 2 glycerol units, sold by the company Solvay;
sorbitan oleate, especially the product sold under the name Span 80 by the company ICI;
sorbitan isostearate, especially the product sold under the name Nikkol SI 10R by the company Nikko;
α-butylglucoside cocoate or α-butylglucoside caprate sold especially by the company Ulice.

3) The mixed esters of C8-C22 fatty acid or of C8-C22 fatty alcohol, of carboxylic acid and of glycerol, which may be used as nonionic amphiphilic lipids in the composition according to the invention may be chosen especially from the group comprising mixed esters of fatty acid or of fatty alcohol with an alkyl chain containing from 8 to 22 carbon atoms, and of α-hydroxy acid and/or of succinic acid, with glycerol. The α-hydroxy acid may be, for example, citric acid, lactic acid, glycolic acid or malic acid, and mixtures thereof.

The alkyl chain of the fatty acids or fatty alcohols from which are derived the mixed esters that may be used in the composition of the invention may be linear or branched, and saturated or unsaturated. They may especially be stearate, isostearate, linoleate, oleate, behenate, arachidonate, palmitate, myristate, laurate, caprate, isostearyl, stearyl, linolenyl, oleyl, behenyl, myristyl, lauryl or capryl chains, and mixtures thereof.

As examples of mixed esters that may be used in the composition of the invention, mention may be made of the mixed ester of glycerol and of the mixture of citric acid, lactic acid, linoleic acid and oleic acid (CTFA name: glyceryl citrate/lactate/linoleate/oleate) sold by the company Hüls under the name Imwitor 375; the mixed ester of succinic acid and of isostearyl alcohol with glycerol (CTFA name: isostearyl diglyceryl succinate) sold by the company Hills under the name Imwitor 780 K; the mixed ester of citric acid and stearic acid with glycerol (CTFA name: glyceryl stearate citrate) sold by the company Hüls under the name Imwitor 370; the mixed ester of lactic acid and stearic acid with glycerol (CTFA name: glyceryl stearate lactate) sold by the company Danisco under the name Lactodan B30 or Rylo LA30.

4) The fatty acid esters of sugars that may be used as nonionic amphiphilic lipids in the composition according to the invention are preferably solid at a temperature of less than or equal to 45° C. and may be chosen especially from the group comprising esters or mixtures of esters of C8-C22 fatty acids and of sucrose, maltose, glucose or fructose, and esters or mixtures of esters of C14-C22 fatty acids and of methylglucose.

The C8-C22 or C14-C22 fatty acids forming the fatty unit of the esters that may be used in the composition of the invention comprise a saturated or unsaturated linear alkyl chain, of 8 to 22 or of 14 to 22 carbon atoms, respectively. The fatty unit of the esters may be chosen especially from stearates, behenates, arachidonates, palmitates, myristates, laurates and caprates, and mixtures thereof. Stearates are especially used.

Examples of esters or mixtures of esters of fatty acid and of sucrose, maltose, glucose or fructose that may be mentioned include sucrose monostearate, sucrose distearate and sucrose tristearate, and mixtures thereof, such as the products sold by the company Croda under the name Crodesta F50, F70, F110 and F160, respectively having an HLB (Hydrophilic-Lipophilic Balance) of 5, 7, 11 and 16; and an example of esters or mixtures of esters of fatty acid and of methylglucose that may be mentioned is methylglucose polyglyceryl-3 distearate, sold by the company Goldschmidt under the name Tegocare 450. Mention may also be made of monoesters of glucose or of maltose such as methyl O-hexadecanoyl-6-D-glucoside and O-hexadecanoyl-6-D-maltoside.

The fatty alkyl ethers of sugars that may be used as nonionic amphiphilic lipids in the composition according to the invention are solid at a temperature of less than or equal to 45° C. and may be chosen especially from the group comprising ethers or mixtures of ethers of C8-C22 fatty alcohol and of glucose, maltose, sucrose or fructose, and ethers or mixtures of ethers of C14-C22 fatty alcohol and of methylglucose. They are especially alkylpolyglucosides.

The C8-C22 or C14-C22 fatty alcohols forming the fatty unit of the ethers that may be used in the composition of the invention comprise a saturated or unsaturated linear alkyl chain containing, respectively, from 8 to 22 or from 14 to 22 carbon atoms. The fatty unit of the ethers may be chosen especially from decyl, cetyl, behenyl, arachidyl, stearyl, palmityl, myristyl, lauryl, capryl and hexadecanoyl units, and mixtures thereof such as cetearyl.

Examples of fatty alkyl ethers of sugars that may be mentioned include alkylpolyglucosides such as decyl glucoside and lauryl glucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of the mixture of arachidyl and behenyl alcohols and of arachidyl glucoside, sold under the name Montanov 202 by the company SEPPIC.

Sucrose monostearate, sucrose distearate, sucrose tristearate and mixtures thereof, methylglucose polyglyceryl-3 distearate and alkylpolyglucosides are more particularly used as fatty acid ester of sugars and as fatty alkyl ethers of sugars.

5) The fatty esters of glycerol that may be used as nonionic amphiphilic lipids in the composition according to the invention, which are solid at a temperature less than or equal to 45° C., may be chosen especially from the group comprising the esters formed from at least one acid comprising a saturated linear alkyl chain containing from 16 to 22 carbon atoms and from 1 to 10 glycerol units. One or more of these fatty esters of glycerol may be used in the composition of the invention.

These esters may be chosen especially from stearates, behenates, arachidates and palmitates, and mixtures thereof. Stearates and palmitates are preferably used.

As examples of fatty esters of glycerol that may be used in the composition of the invention, mention may be made of decaglyceryl monostearate, distearate, tristearate and pentastearate (CTFA names: polyglyceryl-10 stearate, polyglyceryl-10 distearate, polyglyceryl-10 tristearate and polyglyceryl-10 pentastearate), such as the products sold under the respective names Nikkol Decaglyn 1-S, 2-S, 3-S and 5-S by the company Nikko and diglyceryl monostearate (CTFA name: polyglyceryl-2 stearate), such as the product sold by the company Nikko under the name Nikkol DGMS.

The fatty esters of sorbitan that may be used as nonionic amphiphilic lipids in the composition according to the invention are solid at a temperature equal to 45° C. and are chosen especially from the group comprising esters of C16-C22 fatty acid and of sorbitan and oxyethylenated esters of C16-C22 fatty acid and of sorbitan. They are formed from at least one fatty acid comprising at least one saturated linear alkyl chain containing, respectively, from 16 to 22 carbon atoms and from sorbitol or ethoxylated sorbitol. The oxyethylenated esters generally comprise from 1 to 100 ethylene glycol units and preferably from 2 to 40 ethylene oxide (EO) units.

These esters may be chosen especially from stearates, behenates, arachidates and palmitates, and mixtures thereof. Stearates and palmitates are preferably used.

As examples of fatty esters of sorbitan that may be used in the composition of the invention, mention may be made of sorbitan monostearate (CTFA name: sorbitan stearate) sold by the company ICI under the names Span 60, sorbitan monopalmitate (CTFA name: sorbitan palmitate) sold by the company ICI under the name Span 40, and sorbitan 20 EO tristearate (CTFA name: polysorbate 65) sold by the company ICI under the name Tween 65.

The ethoxylated fatty ethers that are solid at a temperature equal to 45° C., which may be used as nonionic amphiphilic lipids in the composition according to the invention, are preferably ethers formed from 1 to 100 ethylene oxide units and from at least one fatty alcohol chain containing from 16 to 22 carbon atoms. The fatty chain of the ethers may be chosen especially from behenyl, arachidyl, stearyl and cetyl units, and mixtures thereof, such as cetearyl. Examples of ethoxylated fatty ethers that may be mentioned include behenyl alcohol ethers comprising 5, 10, 20 and 30 ethylene oxide units (CTFA names: beheneth-5, beheneth-10, beheneth-20, beheneth-30), such as the products sold under the names Nikkol BBS, BB10, BB20 and BB30 by the company Nikko, and stearyl alcohol ether comprising 2 ethylene oxide units (CTFA name: steareth-2), such as the product sold under the name Brij 72 by the company ICI.

The ethoxylated fatty esters that are solid at a temperature less than or equal to 45° C., which may be used as nonionic amphiphilic lipids in the composition according to the invention are esters formed from 1 to 100 ethylene oxide units and from at least one fatty acid chain containing from 16 to 22 carbon atoms. The fatty chain of the esters may be chosen especially from stearate, behenate, arachidate and palmitate units, and mixtures thereof. Examples of ethoxylated fatty esters that may be mentioned include stearic acid ester comprising 40 ethylene oxide units, such as the product sold under the name Myrj 52 (CTFA name: PEG-40 stearate) by the company ICI, and also the behenic acid ester comprising 8 ethylene oxide units (CTFA name: PEG-8 behenate), such as the product sold under the name Compritol HD5 ATO by the company Gattefosse.

6) The block copolymers of ethylene oxide (A) and of propylene oxide (B) that may be used as nonionic amphiphilic lipids in the composition according to the invention may be chosen especially from the block copolymers of formula (IV):

$$HO(C_2H_4O)_x(C_3H_6O)_y(C_2H_4O)_zH \qquad (IV)$$

in which x, y and z are integers such that x+z ranges from 2 to 100 and y ranges from 14 to 60, and mixtures thereof, and more particularly from the block copolymers of formula (I) with an HLB value ranging from 2 to 16.

These block copolymers may be chosen especially from poloxamers and especially from poloxamer 231, such as the product sold by the company ICI under the name Pluronic L81 of formula (I) with x=z=6, y=39 (HLB 2); poloxamer 282, such as the product sold by the company ICI under the name Pluronic L92 of formula (I) with x=z=10, y=47 (HLB 6); and poloxamer 124, such as the product sold by the company ICI under the name Pluronic L44 of formula (I) with x=z=11, y=21 (HLB 16).

Among the nonionic amphiphilic lipids that are preferably used are:
 polyethylene glycol isostearate (8 mol of ethylene oxide),
 diglyceryl isostearate,
 polyglyceryl monolaurate monostearate comprising 10 glycerol units,
 sorbitan oleate, and
 sorbitan isostearate.

The nonionic amphiphilic lipid(s) generally represent from 0.1% to 30%, preferably from 0.5% to 20% and better still from 1% to 10% by weight relative to the total weight of the composition.

Depending on their nature, more hydrophilic or more lipophilic, the nonionic amphiphilic lipid(s) may be introduced into the aqueous phase or into the oily phase of the nanoemulsion.

The weight ratio of the amount of oil(s) to the amount of nonionic amphiphilic lipid(s) is preferably less than or equal to 7, better still between 0.5 and 7 and even more preferentially less than or equal to 5, and better still between 0.5 and 5. The term "amount of oil(s)" means herein the total amount of oil(s) present in the composition, without including the amount of nonionic amphiphilic lipid or the amount of volatile linear alkanes.

According to one particular form of the invention, the composition according to the invention may also comprise one or more cationic and/or anionic amphiphilic lipids. The cationic and/or anionic amphiphilic lipid(s) are not included in the amount of oil for the evaluation of the weight ratio of the amount of oil(s) to the amount of nonionic amphiphilic lipid(s).

Thus, the composition according to the invention may also comprise one or more cationic amphiphilic lipids.

The cationic amphiphilic lipid(s) that may be present in the composition of the invention are preferably chosen from the group formed by quaternary ammonium salts and fatty amines, and salts thereof.

Examples of quaternary ammonium salts include:
 those of general formula (V) below:

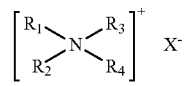

in which the radicals R1 to R4, which may be identical or different, represent a linear or branched aliphatic radical containing from 1 to 30 carbon atoms, or an aromatic radical such as aryl or alkylaryl, at least one of the radicals R1 to R4 containing from 8 to 30 and preferably from 12 to 24 carbon atoms. The aliphatic radicals can comprise heteroatoms such as, in particular, oxygen, nitrogen, sulfur or halogens. The aliphatic radicals are chosen, for example, from alkyl, alkoxy, polyoxy(C2-C6)alkylene, alkylamide, (C12-C22)alkylamido(C2-C6)alkyl, (C12-C22)alkylacetate and hydroxyalkyl radicals, comprising from about 1 to 30 carbon atoms; X is an anion chosen from the group of halides, phosphates, acetates, lactates, (C2-C6)alkyl sulfates and alkyl or alkylaryl sulfonates,
 quaternary ammonium salts of imidazolinium, such as, for example, the salt of formula (VI) below:

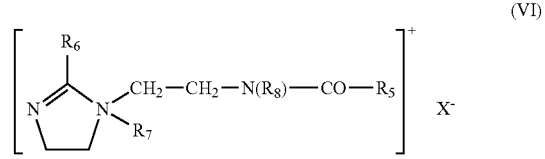

in which R5 represents an alkenyl or alkyl radical containing from 8 to 30 carbon atoms, for example tallow fatty acid derivatives, R6 represents a hydrogen atom, a C1-C4 alkyl radical or an alkenyl or alkyl radical containing from 8 to 30 carbon atoms, R7 represents a C1-C4 alkyl radical, R8 represents a hydrogen atom or a C1-C4 alkyl radical, X is an anion chosen from the group of halides, phosphates, acetates, lactates, alkyl sulfates and alkyl or alkylaryl sulfonates. R5 and R6 preferably denote a mixture of alkenyl or alkyl radicals containing from 12 to 21 carbon atoms, for example tallow fatty acid derivatives, R7 denotes a methyl radical and R8 denotes a hydrogen atom. Such a product is sold, for example, under the name Rewoquat W 75 by the company Rewo;
 diquaternary ammonium salts of formula (VII):

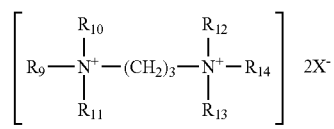

in which R9 denotes an aliphatic radical containing from about 16 to 30 carbon atoms, R10, R11, R12, R13 and R14, which may be identical or different, are chosen from hydrogen or an alkyl radical containing from 1 to 4 carbon atoms, and X is an anion chosen from the group of halides, acetates, phosphates, nitrates and methyl sulfates. Such diquaternary ammonium salts in particular comprise propane tallow diammonium dichloride;
 quaternary ammonium salts containing at least one ester function.

The quaternary ammonium salts containing at least one ester function that may be used according to the invention are, for example, those of formula (VIII) below:

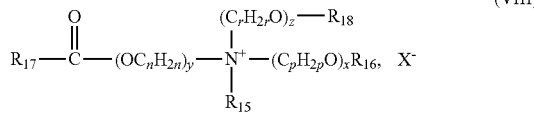

in which:
R15 is chosen from C1-C6 alkyl radicals and C1-C6 hydroxyalkyl or dihydroxyalkyl radicals;
R16 is chosen from:
a radical

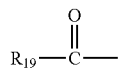

linear or branched, saturated or unsaturated C1-C22 hydrocarbon-based radicals R20,
a hydrogen atom,
R18 is chosen from:

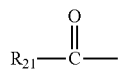

a radical
linear or branched, saturated or unsaturated C1-C6 hydrocarbon-based radicals R22,
a hydrogen atom,
R17, R19 and R21, which may be identical or different, are chosen from linear or branched, saturated or unsaturated C7-C21 hydrocarbon-based radicals;
n, p and r, which may be identical or different, are integers ranging from 2 to 6;
y is an integer ranging from 1 to 10;
x and z, which may be identical or different, are integers ranging from 0 to 10;
X— is a simple or complex, organic or inorganic anion;
with the proviso that the sum x+y+z is from 1 to 15, that when x is 0, then R16 denotes R20 and that when z is 0, then R18 denotes R22.

The R15 alkyl radicals may be linear or branched and more particularly linear.

R15 preferably denotes a methyl, ethyl, hydroxyethyl or dihydroxypropyl radical and more particularly a methyl or ethyl radical.

The sum x+y+z is advantageously from 1 to 10.

When R16 is a hydrocarbon-based radical R20, it may be long and contain from 12 to 22 carbon atoms, or short and contain from 1 to 3 carbon atoms.

When R18 is a hydrocarbon-based radical R22, it preferably contains 1 to 3 carbon atoms.

R17, R19 and R21, which may be identical or different, are advantageously chosen from linear or branched, saturated or unsaturated C11-C21 hydrocarbon-based radicals, and more particularly from linear or branched, saturated or unsaturated, C11-C21 alkyl and alkenyl radicals.

x and z, which may be identical or different, are preferably 0 or 1.

y is advantageously equal to 1.

n, p and r, which may be identical or different, are preferably 2 or 3 and even more particularly are equal to 2.

The anion is preferably a halide (chloride, bromide or iodide) or an alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function, may be used.

The anion X— is even more particularly chloride or methyl sulfate.

The ammonium salts more particularly used are those of formula (VIII) in which:
R15 denotes a methyl or ethyl radical,
x and y are equal to 1;
z is equal to 0 or 1;
n, p and r are equal to 2;
R16 is chosen from:
a radical

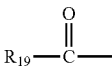

methyl, ethyl or C14-C22 hydrocarbon-based radicals;
a hydrogen atom;
R18 is chosen from:
a radical

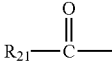

a hydrogen atom;
R17, R19 and R21, which may be identical or different, are chosen from linear or branched, saturated or unsaturated C13-C17 hydrocarbon-based radicals and preferably from linear or branched, saturated or unsaturated C13-C17 alkyl and alkenyl radicals.

The hydrocarbon-based radicals are advantageously linear.

Examples of compounds of formula (VIII) that may be mentioned include the diacyloxyethyldimethylammonium, diacyloxyethylhydroxyethylmethylammonium, mono-acyloxyethyldihydroxyethylmethylammoniurn, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart by the company Henkel, Stepanquat by the company Stepan, Noxamium by the company CECA or Rewoquat WE 18 by the company Rewo-Witco.

The composition according to the invention preferably contains a quaternary ammonium salt of formula (V).

Among the quaternary ammonium salts of formula (V) that are preferred are, on the one hand, tetraalkylammonium chlorides, for instance dialkyldimethylammonium or alkyltrimethylammonium chlorides in which the alkyl radical contains from about 12 to 22 carbon atoms, in particular behenyltrimethylammonium chloride, distearyl-dimethylammonium chloride, cetyltrimethylammonium chloride or benzyl-dimethylstearylammonium chloride, or, on the other hand, stearamidopropyl-dimethyl(myristyl acetate)ammonium chloride sold under the name Ceraphyl 70 by the company Van Dyk.

According to the invention, behenyltrimethylammonium chloride and cetyltrimethylammonium chloride are the quaternary ammonium salts that are the most particularly preferred.

The composition according to the invention may also comprise one or more anionic amphiphilic lipids.

The anionic amphiphilic lipid(s) that may be present in the composition according to the invention may especially be chosen from:
  alkyl ether citrates,
  alkoxylated alkenyl succinates,
  alkoxylated glucose alkenyl succinates,
  alkoxylated methylglucose alkenyl succinates,
  alkali metal salts of dicetyl and dimyristyl phosphate,
  alkali metal salts of cholesteryl sulfate,
  alkali metal salts of cholesteryl phosphate,
    lipoamino acids and salts thereof such as monosodium and disodium acylglutamates, for instance the disodium salt of N-stearoyl-L-glutamic acid sold under the name Acylglutamate HS21 by the company Ajinomoto,
    the sodium salts of phosphatidic acid,
    phospholipids,
    alkylsulfonic or alkyl ether sulfonic derivatives.

The alkyl ether citrates that may be used as anionic amphiphilic lipids in the composition according to the invention may be chosen especially from the group comprising monoesters, diesters or triesters formed from citric acid and at least one oxyethylenated fatty alcohol, comprising a linear or branched, saturated or unsaturated alkyl chain containing from 8 to 22 carbon atoms, and comprising from 3 to 9 ethoxyl groups, and mixtures thereof. A mixture of one or more of these citrates may effectively be used in the composition of the invention.

These citrates may be chosen, for example, from mono-, di- and triesters of citric acid and of ethoxylated lauryl alcohol, comprising from 3 to 9 ethoxyl groups, sold by the company Witco under the name Witconol EC, in particular Witconol EC 2129, which is predominantly a dilaureth-9 citrate, and Witconol EC 3129, which is predominantly a trilaureth-9 citrate.

The alkyl ether citrates used as surfactants are preferably used in a form neutralized to a pH of about 7, the neutralizer being chosen from mineral bases such as sodium hydroxide, potassium hydroxide or ammonia, and organic bases such as monoethanolamine, diethanolamine, triethanolamine, aminomethyl-1,3-propanediol or N-methylglucamine, and basic amino acids, for instance arginine and lysine, and mixtures thereof.

The alkenyl succinates that may be used as anionic amphiphilic lipids in the composition of the invention are especially ethoxylated and/or propoxylated derivatives and are preferably chosen from the compounds of formula (IX) or (X):

HOOC—(HR)C—CH2-COO-E           (IX)

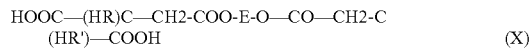

HOOC—(HR)C—CH2-COO-E-O—CO—CH2-C(HR')—COOH           (X)

in which:
  the radicals R and R' are chosen from linear or branched alkenyl radicals containing from 6 to 22 carbon atoms,
  E is chosen from oxyethylenated chains of formula (C2H4O)n in which n ranges from 2 to 100, oxypropylenated chains of formula (C3H6O)n in which n' ranges from 2 to 100, statistical or block copolymers comprising oxyethylenated chains of formula (C2H4O)n and oxypropylenated chains of formula (C3H6O)n' such that the sum of n and n' ranges from 2 to 100, oxyethylenated and/or oxypropylenated glucose groups comprising on average from 4 to 100 oxyethylene and/or oxypropylene units distributed throughout the hydroxyl functions, and oxyethylenated and/or oxypropylenated methylglucose groups comprising on average from 4 to 100 oxyethylene and/or oxypropylene units distributed throughout the hydroxyl functions.

In formulae (IX) and (X), n and n' are mean values and are therefore not necessarily integers. A value ranging from 5 to 60 and even more preferentially from 10 to 30 is advantageously chosen for n.

Advantageously, the radical R and/or R' is chosen from linear alkenyl radicals containing from 8 to 22 and preferably from 14 to 22 carbon atoms. It may be, for example, a hexadecenyl radical containing 16 carbon atoms or an octadecenyl radical containing 18 carbon atoms.

The compounds of formulae (IX) and (X) described above in which E is chosen from oxyethylene chains, oxypropylene chains and copolymers comprising oxyethylene chains and oxypropylene chains may be prepared in accordance with the description given in documents WO-A-94/00508, EP-A-107 199 and GB-A-2 131 820, which are incorporated herein for reference.

The acid function —COOH of the anionic amphiphilic lipids of formulae (IX) and (X) are generally present in the composition of the invention in a form neutralized with a neutralizer, the neutralizer being chosen, for example, from mineral bases such as sodium hydroxide, potassium hydroxide or ammonia, and organic bases such as monoethanolamine, diethanolamine, triethanolamine, aminomethyl-1,3-propanediol or N-methylglucamine, and basic amino acids, for instance arginine and lysine, and mixtures thereof.

As examples of anionic amphiphilic lipids that may be used in the composition of the invention, mention may be made of hexadecenyl succinate 18 EO (compound of formula I with R=hexadecenyl, E=(C2H4O)n, n=18), hexadecenyl succinate 45 EO (compound of formula I with R=hexadecenyl, E=(C2H4O)n, n=45), dihexadecenyl succinate 18 EO (compound of formula II with R=R'=hexadecenyl, E=(C2H4O)n, n=18), glucose dihexadecenyl succinate 10 EO (compound of formula II with R=R'=hexadecenyl, E=oxyethylenated glucose comprising 10 oxyethylene groups), glucose dihexadecenyl succinate 20 EO (compound of formula II with R=R'=hexadecenyl, E=oxyethylenated glucose comprising 20 oxyethylene groups), methylglucose dioctadecenyl succinate 20 EO (compound of formula II with R=R'=octadecenyl, E=oxyethylenated methylglucose comprising 20 oxyethylene groups), and mixtures thereof.

The cationic and/or anionic amphiphilic lipid(s) that may be present in the composition according to the invention may represent from 0.1% to 15% and preferably from 0.2% to 5% by weight relative to the total weight of the composition.

Preferably, the compositions of the invention comprise one or more cationic amphiphilic lipids.

The cosmetic composition according to the invention may also comprise one or more polymers.

The polymer(s) may be of natural, plant, mineral and/or synthetic origin.

For the purposes of the present invention, the term "polymer" means a compound comprising a repetition of at least two units derived from at least one compound referred to as a monomer. This thus includes oligomers with a repetition number ranging from 2 to 10.

The polymers of natural origin may be chosen from pectins, celluloses, alginates, galactoarabinan, gum tragacanth, starches and sucrose.

The synthetically modified polymers of plant origin may be chosen, for example, from starch derivatives, such as carboxymethylstarch and distarch phosphate, and cellulose derivatives such as hydroxyethylcellulose and carboxymethylcellulose.

The polymers may be chosen from cationic, anionic, amphoteric and nonionic polymers.

Preferably, the ionic polymers are of cationic nature.

For the purposes of the present invention, the term "cationic polymer" means any polymer comprising cationic groups and/or groups that may be ionized into cationic groups.

The cationic polymers that may be used according to the present invention are preferably chosen from polymers comprising primary, secondary, tertiary and/or quaternary amine groups forming part of the polymer chain or directly attached thereto, and having a number average molecular weight of between 500 and about 5 000 000 and preferably between 1000 and 3 000 000.

Among these polymers, mention may be made more particularly of the following cationic polymers:

(1) homopolymers or copolymers derived from acrylic or methacrylic esters or amides with amine functions, and comprising at least one of the units of the following formulae:

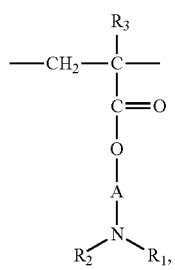

(A)

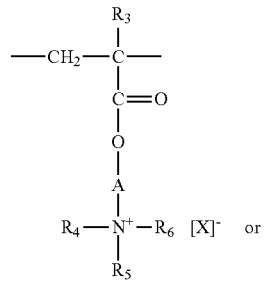

(B)

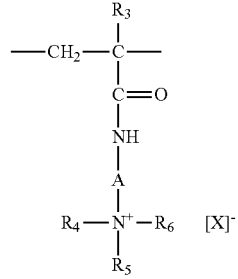

(C)

in which:
R1 and R2, which may be identical or different, each represent a hydrogen atom or an alkyl group having from 1 to 6 carbon atoms;
R3 denotes a hydrogen atom or a group CH3;
A is a linear or branched alkyl group comprising 1 to 6 carbon atoms or a hydroxyalkyl group comprising 1 to 4 carbon atoms;
R4, R5 and R6, which may be identical or different, represent an alkyl group having from 1 to 18 carbon atoms or a benzyl group;
X denotes a methosulfate anion or a halide such as chloride or bromide.

The copolymers of the family (1) also contain one or more comonomer units that may be chosen from the family of acrylamides, methacrylamides, diacetone acrylamides, acrylamides and methacrylamides substituted on the nitrogen with lower (C1-4) alkyl groups, groups derived from acrylic or methacrylic acids or esters thereof, vinyllactams such as vinylpyrrolidone or vinylcaprolactam, and vinyl esters.

Thus, among these copolymers of the family (1), mention may be made of:
  copolymers of acrylamide and of dimethylaminoethyl methacrylate quaternized with dimethyl sulfate or with a dimethyl halide, such as the one sold under the name Hercofloc® by the company Hercules,
  copolymers of acrylamide and of methacryloyloxyethyltrimethylammonium chloride, described, for example, in patent application EP-A-080 976 and sold under the name Bina Quat P 100 by the company Ciba Geigy,
  copolymers of acrylamide and of methacryloyloxyethyltrimethylammonium methosulfate, such as the product sold under the name Reten by the company Hercules,
  quaternized or non-quaternized vinylpyrrolidone/dialkylaminoalkyl acrylate or methacrylate copolymers, such as the products sold under the name Gafquat® by the company ISP, such as, for example, Gafquat® 734 or Gafquat® 755, or alternatively the products known as Copolymer® 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, such as the product sold under the name Gafquat® HS 100 by the company ISP;

crosslinked polymers of methacryloyloxy(C1-C4)alkyltri (C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the copolymer in mineral oil can be used more particularly. This dispersion is sold under the name Salcare® SC 92 by the company Ciba. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Ciba.

(2) cationic polysaccharides, and in particular those chosen from:

a) cellulose ether derivatives containing quaternary ammonium groups, described in French patent 1 492 597. These polymers are also defined in the CTFA dictionary as quaternary ammoniums of hydroxyethylcellulose that have reacted with an epoxide substituted with a trimethylammonium group;

b) cellulose derivatives grafted with a water-soluble monomer of quaternary ammonium, and described especially in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacryl-amidopropyltrimethylammonium or dimethyldiallylammonium salt.

The commercial products corresponding to this definition are more particularly the products sold under the names Celquat L 200 and Celquat H 100 by the company National Starch.

c) cationic polygalactomannans such as those described in U.S. Pat. Nos. 3,589,578 and 4,031,307, such as guar gums containing cationic trialkylammonium groups. Such products are sold in particular under the trade names Jaguar C13 S, Jaguar C 15 and Jaguar C 17 by the company Meyhall.

(3) quaternary copolymers of vinylpyrrolidone and of vinylimidazole.

(4) dialkyldiallylammonium halide homopolymers or copolymers and in particular the compounds sold the company Nalco under the names Merquat 100, Merquat 7SPR and Merquat 550.

(5) chitosans or salts thereof; the salts that can be used are, in particular, chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

The polymer(s) generally represent from 0 to 20% and preferably from 0.2% to 10% by weight relative to the total weight of the composition.

The composition according to the invention comprises a cosmetically acceptable medium.

This medium is preferably aqueous, i.e. it comprises either water alone, or water and one or more solvents, for instance ethanol, propylene glycol, butylene glycol, isopropanol, glycerol, glycol ethers such as mono-, di- or tripropylene glycol (C1-C4)alkyl ethers, mono-, di- or triethylene glycol, or dipropylene glycol, and mixtures thereof.

The composition according to the invention may also comprise any additive that may be used in the field of application under consideration.

The emulsions of the invention may contain water-soluble or liposoluble active agents with cosmetic or dermopharmaceutical activity. The liposoluble active agents are in the oil globules of the emulsion, while the water-soluble active agents are in the aqueous phase of the emulsion. Examples of active agents that may be mentioned include vitamins and derivatives thereof such as vitamin E, vitamin E acetate, vitamin C and esters thereof, B vitamins, vitamin A alcohol or retinol, vitamin A acid or retinoic acid and derivatives thereof, provitamins such as panthenol, vitamin A palmitate, niacinamide, ergocalciferol, antioxidants, humectants, silicone or non-silicone sunscreens, preserving agents, sequestrants, softeners, dyes, viscosity modifiers, foam modifiers, foam stabilizers, nacreous agents, pigments, moisturizers, antidandruff agents, anti-seborrhoeic agents, proteins, ceramides, pseudoceramides, fatty acids containing linear or branched C16-C40 chains such as 18-methyleicosanoic acid, plasticizers, hydroxy acids, electrolytes and fragrances.

The nanoemulsions of the invention may be obtained via a process wherein the aqueous phase and the oily phase are mixed together, with vigorous stirring, at an ambient temperature below 45° C., and high-pressure homogenization is then performed at a pressure above $5 \times 10^7$ Pa, preferably ranging from $6 \times 10^7$ to $18 \times 10^7$ Pa. Such a process makes it possible to produce, at room temperature, nanoemulsions that are compatible with heat-sensitive active compounds, and that may contain large amounts of oils and especially fragrances that contain fatty substances, without denaturing them.

They may also be obtained via a dilution process as described in patent application FR 2 847 831.

A subject of the invention is also the use of the composition as defined previously for conditioning the hair.

The invention is illustrated by the examples that follow.

Example 1

Various compositions in nanoemulsion form are prepared. The formulations are given in Table 1. The contents are expressed in grams of product per se per 100 grams of composition.

Composition 1 is not a composition according to the invention.

Composition 2 is a composition according to the invention.

TABLE 1

| | 1 | 2 |
|---|---|---|
| Liquid jojoba wax | 6 | 6 |
| Avocado oil | 5 | 5 |
| Cyclopentadimethylsiloxane (Dow Corning) | 3 | |
| Undecane/tridecane mixture according to Example 2 of WO 2008/155 059 | | 3 |

TABLE 1-continued

|  | 1 | 2 |
|---|---|---|
| Polydimethylsiloxane containing aminoethyl iminopropyl groups, as a nonionic microemulsion at 17% in water (Wacker) | 5 | 5 |
| 96° Ethanol | 17 | 17 |
| Glycerol | 4 | 4 |
| Behenyltrimethylammonium chloride at 79% (Clariant) | 2 | 2 |
| Polyethylene glycol monoisostearate (8 OE) (Croda) | 3 | 3 |
| Fragrance | qs | |
| Deionized water | qs 100 | |

The viscosity of compositions 1 and 2 is measured using a Brookfield DVII+Pro viscometer, at 25° C. The reading is taken at one minute. The results are given in cps, in Table 2.

TABLE 2

|  | Composition | |
|---|---|---|
|  | 1 | 2 |
| Viscosity in cps | 135 | 8500 |

The volatile linear alkanes give greater thickening than the other solvents conventionally used, such as cyclopentadimethylsiloxane.

Example 2

Various compositions in nanoemulsion form are prepared. The formulations are given in Table 3. The contents are expressed in grams of product per se per 100 grams of composition.

Compositions 3 and 4 are compositions according to the invention.

TABLE 3

|  | 3 | 4 |
|---|---|---|
| Liquid jojoba wax | 6 | 6 |
| Stabilized avocado oil | 5 | 5 |
| n-Undecane/n-tridecane mixture according to Example 2 of WO 2008/155 059 | 3 | |
| n-Dodecane/n-tetradecane mixture (Vegelight 1214 from Biosynthis) | | 3 |
| Polydimethylsiloxane containing aminoethyl iminopropyl groups, as a nonionic microemulsion at 17% in water (Wacker) | 5 | 5 |
| 96° Ethanol | 17 | 17 |
| Glycerol | 4 | 4 |
| Behenyltrimethylammonium chloride at 79% (Clariant) | 2 | 2 |
| Polyethylene glycol monoisostearate (8 OE) (Croda) | 2 | 3 |
| Fragrance | qs | |
| Deionized water | qs 100 | |

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A cosmetic composition in the form of an oil-in-water nanoemulsion comprising, in a cosmetically acceptable medium, one or more nonionic amphiphilic lipids, two or more volatile linear alkanes in an amount of from 2 to 15% by weight relative to the total weight of the composition, and one or more oils other than the volatile linear alkane(s),
   wherein two volatile linear alkanes comprise from 10 to 14 carbon atoms and differ from each other by a carbon number of at least 2.

2. The composition according to claim 1, wherein the two volatile linear alkane(s) are of plant origin.

3. The composition according to claim 1, wherein the two volatile linear alkane(s) are chosen from n-decane, n-undecane, n-dodecane, n-tridecane and n-tetradecane.

4. The composition according to claim 1, wherein the two volatile linear alkane(s) are chosen from n-undecane, n dodecane, n-tridecane and n-tetradecane.

5. The composition according to claim 4, wherein the two volatile linear alkanes are an n-undecane and n-tridecane.

6. The composition according to claim 1, wherein the nonionic amphiphilic lipid(s) are chosen from:
   1) silicone surfactants,
   2) amphiphilic lipids that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, and polyglycerols comprising from 2 to 15 glycerol units, and of at least one fatty acid comprising at least one saturated or unsaturated, linear or branched C8-C22 alkyl chain,
   3) mixed esters of C8-C22 fatty acid or of C8-C22 fatty alcohol, of carboxylic acid and of glycerol,
   4) fatty acid esters of sugars and fatty alkyl ethers of sugars,
   5) surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters, and
   6) block copolymers of ethylene oxide (A) and of propylene oxide (B).

7. The composition according to claim 6, wherein the nonionic amphiphilic lipid(s) are chosen from:
   polyethylene glycol isostearate (8 mol of ethylene oxide),
   diglyceryl isostearate,
   polyglyceryl monolaurate and monostearate comprising 10 glycerol units,
   sorbitan oleate,
   sorbitan isostearate.

8. The composition according to claim 1, wherein the nonionic amphiphilic lipid(s) represent from 0.1% to 30% by weight relative to the total weight of the composition.

9. The composition according to claim 1, wherein the oil(s) are chosen from plant oils, animal oils, mineral oils, synthetic oils, liquid fatty alcohols and silicone oils, and mixtures thereof.

10. The composition according to claim 1, wherein the oil(s) are present in an amount ranging from 1% to 40% by weight relative to the total weight of the composition.

11. The composition according to claim 1, further comprising one or more cationic amphiphilic lipids.

12. The composition according to claim 1, wherein the weight ratio of the amount of oil(s) to the amount of nonionic amphiphilic lipid(s) is less than or equal to 7.

13. A method for conditioning hair, comprising applying the composition of claim 1 to hair.

14. A cosmetic composition in the form of an oil-in-water nanoemulsion comprising, in a cosmetically acceptable medium, one or more nonionic amphiphilic lipids, two volatile linear alkanes in an amount of from 2 to 15% by weight relative to the total weight of the composition, and one or more oils other than the volatile linear alkane(s),
   wherein two volatile linear alkanes comprise from 10 to 14 carbon atoms and differ from each other by a carbon number of 2.

* * * * *